United States Patent [19]

Geurts et al.

[11] 4,153,600

[45] May 8, 1979

[54] PROCESS FOR THE RECOVERY OF ε-CAPROLACTAM FROM A DISTILLATION RESIDUE CONTAINING ε-CAPROLACTAM

[75] Inventors: Gerardus A. Geurts, Schaesberg; Reijer Goettsch, Beek(L), both of Netherlands

[73] Assignee: Stamicarbon, B.V., Geleen, Netherlands

[21] Appl. No.: 865,338

[22] Filed: Dec. 28, 1977

[30] Foreign Application Priority Data

Jan. 12, 1977 [NL] Netherlands ............... 7700234

[51] Int. Cl.² ............................................. C07D 201/16
[52] U.S. Cl. ............................................. 260/239.3 A
[58] Field of Search ................................ 260/239.3 A

[56] References Cited

U.S. PATENT DOCUMENTS

| | | | |
|---|---|---|---|
| 2,221,396 | 11/1940 | Cass | 260/239.3 A |
| 2,758,991 | 8/1956 | Kretzers et al. | 260/239.3 A |
| 3,852,272 | 12/1974 | De Rooij et al. | 260/239.3 A |

Primary Examiner—Natalie Trousof
Assistant Examiner—Robert T. Bond
Attorney, Agent, or Firm—Cushman, Darby & Cushman

[57] ABSTRACT

A method of recovering ε-caprolactam from the residue remaining from the distillation of impure ε-caprolactam wherein the residue is treated with sulphuric acid or oleum at a temperature between about 80° C. and about 140° C. and the resultant mixture neutralized. The lactam is then extracted with an organic solvent with the lactam then recovered from the resultant solution.

2 Claims, No Drawings

PROCESS FOR THE RECOVERY OF ε-CAPROLACTAM FROM A DISTILLATION RESIDUE CONTAINING ε-CAPROLACTAM

The invention relates to a process for the recovery of ε-caprolactam from a residue that remains in the distillation of impure ε-caprolactam.

In various methods for the preparation of caprolactam in a pure state, distillation is used as part of the purification processes (see, e.g., U.S. Pat. No. 2,758,991). The highly contaminated residue then obtained contains such an amount of caprolactam that processing the residue is highly important to the economy of the caprolactam process in question. This processing can, in principle, be done by returning the residue to the main product flow to be purified, e.g. if in the preparation of caprolactam a mixture of lactam and sulphuric acid is neutralized with ammonia, by adding the residue to the neutralized mixture to be purified. However, the return of the residue involves a considerable enlargement of the required purifying installation, while the resulting final product moreover has a slightly poorer purity than can be obtained without returning the residue, because a comparatively large amount of impurities is returned. According to U.S. Pat. No. 3,839,324, which describes a combination of a distillation and a melt crystallization for the purification of caprolactam, the distillation residue is first extracted with benzene or toluene and the resulting solution containing lactam is then returned to the main product flow to be purified. This way of returning the distillation residue seems hardly better than the abovementioned method of returning.

A very suitable method for the recovery of pure lactam from the distillation residue has now been found in which the above drawbacks are obviated. The process according to the invention for the recovery of ε-caprolactam from the residue remaining in the distillation of impure ε-caprolactam is characterized in that the residue is treated with sulphuric acid or oleum at a temperature of 80°–140° C., the resulting mixture is fully or partly neutralized, the lactam is extracted from the resulting mixture with an organic solvent, and the lactam is recovered in a known way from the solution thus obtained.

Owing to the treatment of the residue with sulphuric acid or oleum, the impurities appear so to be affected chemically that the recovery of pure caprolactam from the treated residue can be effected in the same way as the recovery of pure caprolactam from a reaction mixture obtained by rearrangement of cyclohexanone oxime with sulphuric acid or oleum.

In the process according to the invention the use of sulphuric acid or oleum is normally restricted as much as possible to reduce the formation of by-product in the neutralization to a minimum. Per gram of residue use is normally made of an amount of sulphuric acid or oleum that corresponds to 1–2.5 grams of sulphur trioxide (bound as sulphuric acid and free sulphur trioxide). A smaller amount of sulphuric acid or oleum may also be used in principle. However, the use of an amount of sulphuric acid or oleum corresponding to less than 0.5 gram of sulphur trioxide per gram of residue is less suitable in practice.

The use of more sulphuric acid or oleum than corresponds to 2.5 grams of sulphur trioxide per gram of residue, e.g. an amount of 5 grams of sulphur trioxide per gram of residue, is quite possible and only results in the formation of more by-product in the neutralization of the treated residue. The residue can also be treated with a comparatively large amount of sulphuric acid or oleum by combining the treatment of the residue with the rearrangement of cyclohexanone oxime into caprolactam with sulphuric acid or oleum, as this rearrangement can be carried out under the same conditions as the residue treatment and the rearrangement mixture obtained can be processed in the same way as the reaction mixture obtained in the treatment of the residue.

The complete or partial neutralization of the residue treatment with sulphuric acid or oleum can very well be effected with ammonia water. Complete neutralization gives ammonium sulphate as a by-product. In partial neutralization the by-product obtained is, e.g., ammonium hydrogen sulphate. Partial neutralization can also be effected with ammonium sulphate instead of with ammonia water.

After the complete or partial neutralization, the lactam is extracted from the resulting mixture with an organic solvent. In the case of complete neutralization benzene or toluene can very well be used for this purpose. In the case of partial neutralization very good results are obtained with chlorinated hydrocarbons, such as chloroform, 1,1,2,2-tetrachlorethane and 1,2-dichloroethane.

The resulting solution of caprolactam in the organic solvent can be processed to recover pure caprolactam in a known way, e.g. as described in the abovementioned U.S. Pat. No. 2,758,991.

The process according to the invention will be further elucidated in the following examples.

EXAMPLE I

As the last of a number of purifying treatments, impure ε-caprolactam was subjected to a distillation at reduced pressure (10 mm of Hg) in the presence of sodium hydroxide. A distillate was obtained which met the usual quality standards. The remaining residue, which contained 95% by weight of ε-caprolactam and 0.16% by weight of sodium hydroxide, had a yellow colour owing to the presence of impurities.

100 Grams of the residue were mixed with 245 grams of oleum (2.8% by weight of free sulphur trioxide) with stirring in period of 5 minutes in a 0.5 liter flask provided with a stirrer. During mixing the reaction mixture was kept at a temperature of 130° C. by cooling the flask on the outside. The resulting mixture was well stirred at this temperature for another 15 minutes. Next, the mixture was neutralized to a pH of 4.5 at 40° C. with ammonia water (15% by weight of $NH_3$), after which the resulting liquid layer containing lactam was separated and extracted with benzene. The solution of caprolactam in benzene obtained (20% by weight of caproactam) was then extracted with water. The aqueous solution thus obtained contained 30% by weight of caprolactam. The extinction of this solution (calculated to 50% by weight of lactam, measured at a layer thickness of 1 cm with light of 290 nanometers and expressed as the logarithm of the amount of light absorbed) was 3. (Removal of ionic impurities from such an aqueous solution can be effected in a known way by means of ion exchangers, as described, e.g., in the abovementioned U.S. Pat. No. 2,758,991).

For the sake of comparison an amount of residue was extracted with benzene without it being treated with oleum and next the resulting solution was subjected to an extraction with water. The extinction of the aqueous solution obtained was 4.5.

EXAMPLE II

100 Grams of a yellow residue obtained in the distillation of caprolactam (98% by weight of caprolactam, 0.3% by weight of NaOH) were mixed with 175 grams of oleum (3.2% by weight of free sulphur trioxide) in the way described in Example I, the temperature being kept at 120° C. and the resulting mixture being stirred at this temperature for 20 more minutes. The reaction mixture was then processed further in the way described in Example I. The aqueous solution obtained had an extinction of 1.5. Repetition of the experiment without the treatment with oleum resulted in an extinction of 2.0.

EXAMPLE III

100 Grams of a yellow residue obtained in the distillation of caprolactam (95% by weight of caprolactam, 0.16% by weight of NaOH) were mixed with 128 grams of oleum (14.4% by weight of free sulphur trioxide) in the way described in Example I, the temperature being kept at 125° C. and the resulting mixture being stirred at 125° C. for 15 more minutes.

Next, ammonia and water were added to the reaction mixture at 20° C. in such quantities that ammonium hydrogen sulphate was obtained as the neutralization product and the amount of water was equal to the amount of ammonium hydrogen sulphate. The caprolactam was extracted from the resulting solution by means of chloroform. The solution then obtained contained 25% by weight of caprolactam.

After neutralization with ammonia and removal of the ammonium salt formed, this solution was concentrated by evaporation to 60% by weight of caprolactam and subjected to an extraction with water. The resulting aqueous solution (30% by weight of caprolactam) had an extinction of 2.1.

We claim:

1. Process for the recovery of $\epsilon$-caprolactam from the residue remaining in the distillation of impure $\epsilon$-caprolactam, characterized in that the residue is treated with sulphuric acid or oleum at a temperature of 80°–140° C., the resulting mixture is fully or partly neutralized, the lactam is extracted from the resulting mixture with an organic solvent, and the lactam is recovered in a known way from the solution thus obtained.

2. The process according to claim 1, wherein the treatment of the residue is combined with the rearrangement of cyclohexanone oxime into caprolactam with sulphuric acid or oleum.

* * * * *